United States Patent
Walmsley et al.

[19]

[11] Patent Number: 5,891,175
[45] Date of Patent: Apr. 6, 1999

[54] METHOD AND APPARATUS FOR RATE-RESPONSIVE CARDIAC PACING

[75] Inventors: Frank R Walmsley, North Oaks; Jan-Pieter Heemels, Minneapolis, both of Minn.

[73] Assignee: Cardiac Pacemakers, St. Paul, Minn.

[21] Appl. No.: 773,877

[22] Filed: Dec. 26, 1996

[51] Int. Cl.$^6$ .................................................. A61N 1/365
[52] U.S. Cl. .............................................................. 607/17
[58] Field of Search ........................... 607/17, 5, 9, 14, 607/18

[56] References Cited

U.S. PATENT DOCUMENTS

| | | |
|---|---|---|
| 3,656,487 | 4/1972 | Gobeli . |
| 4,363,325 | 12/1982 | Roline . |
| 4,428,378 | 1/1984 | Anderson et al. . |
| 4,485,813 | 12/1984 | Anderson et al. . |
| 4,702,253 | 10/1987 | Nappholz et al. . |
| 5,063,927 | 11/1991 | Webb et al. . |
| 5,144,949 | 9/1992 | Olson . |
| 5,271,935 | 12/1993 | Franco et al. ........................... 424/115 |
| 5,374,281 | 12/1994 | Kristall et al. ............................. 607/17 |
| 5,391,189 | 2/1995 | Van Krieken et al. .................... 607/17 |
| 5,409,009 | 4/1995 | Olson ................................. 128/661.08 |

FOREIGN PATENT DOCUMENTS

| | | |
|---|---|---|
| 0559193 | 9/1993 | European Pat. Off. . |
| 0596540 | 5/1994 | European Pat. Off. . |

*Primary Examiner*—Scott M. Getzow
*Attorney, Agent, or Firm*—Schwegman, Lundberg, Woessner & Kluth, P.A.

[57] ABSTRACT

Pacemakers have been known to be provided with a lower rate hysteresis mode in which a range of cardiac activity is supported in a hysteresis loop by a pacemaker. The present invention describes a programmable single or dual chamber pacemaker comprising a sensor device which provides signals indicating a level of cardiac activity. The pacemaker has a standard lower rate hysteresis mode available, but is also provided with a sensor rate hysteresis which may be programmable. The signals from the sensor can cause the pacemaker to operate within a hysteresis loop in which at least one of the A-sense Rate and the V-sense Rate in the sensor rate hysteresis is higher than the similar rate in the lower rate hysteresis.

35 Claims, 4 Drawing Sheets

METHOD AND APPARATUS FOR RATE-RESPONSIVE CARDIAC PACING

FIELD OF THE INVENTION

This invention relates generally to the field or cardiac pacemakers, and more particularly relates to cardiac pacemakers of the type in which signals are generated in response to measurements or conditions as provided by any sensors such as an accelerometer, and in which these signal identify that a pacer must vary the pacing rate of a pacemaker in accordance with the signals and measurements.

A cardiac pacemaker system is described which improves rate control by favoring intrinsic rhythms. Hysteresis is applied to the sensor rate, thus favoring the intrinsic activation and rhythm over the entire range of the sensor rather than just at the lower rate region.

BACKGROUND OF THE INVENTION

A wide variety of cardiac pacemakers are known and commercially available. Pacemakers are generally characterized by a number of different aspects of their construction or use, such as which chambers of the heart they are capable of sensing, the chambers to which they deliver pacing stimuli, and their responses, if any, to sensed intrinsic electrical cardiac activity. Some pacemakers delivery pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. One such pacemaker, for example, senses electrical cardiac activity in the ventricle of the patient's heart, and delivers pacing stimuli to the ventricle only in the absence of electrical signals indicative of natural ventricular contractions. Another type of pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by the second type of pacemaker is synchronized with prior sensed or paced events.

Pacemakers are also known which respond to other types of physiologically-based signals, such as signals from sensors for measuring the pressure inside the patient's ventricle or for measuring the level of the patient's physical activity. In recent years, pacemakers which measure the metabolic demand for oxygen and vary the pacing rate in response thereto have become widely available. Another method for measuring the need for oxygenated blood is to measure the physical activity of the patient by means of a piezoelectric transducer. Such a pacemaker is disclosed in U.S. Pat. Nos. 4,428,378; and 4,485,813 issued to Anderson et al.

In typical prior art rate-responsive pacemakers, the pacing rate is determined according to the output from an activity sensor. The pacing rate is variable between a predetermined maximum and minimum level, which may be selectable from among a plurality of programmable upper and lower rate limit settings. When the activity sensor output indicates that the patient's activity level has increased, the pacing rate is increased from the programmed lower rate by an incremental amount which is determined as a function of the output of the activity sensor. That is, the rate-responsive or "target" pacing rate in a rate-responsive pacemaker is determined as follows:

Target Rate=Programmed Lower Rate+$f$(sensor output)

where f is typically a linear or monotonic function of the sensor output. As long as patient activity continues to be indicated, the pacing rate is periodically increased by incremental amounts calculated according to the above formula, until the programmed upper rate limit is reached. When patient activity decreases, the pacing rate is gradually reduced, until the programmed lower rate limit is reached.

In an effort to minimize patient problems and to prolong or extend the useful life of an implanted pacemaker, it has become common practice to provide numerous programmable parameters to permit a physical examination to select and/or periodically adjust the desired parameters or to match or optimize the pacing system to the patient's physiologic requirements. The physician may adjust the output energy settings to maximize pacemaker battery longevity while ensuring an adequate patient safety margin. Additionally, the physician may adjust the sensing threshold to ensure adequate sensing of intrinsic depolarization of cardiac tissue, while preventing oversensing of unwanted events such as myopotential interferences or electromagnetic interference (EMI). Also, programmable parameters are typically required to enable and to optimize the rate response function of a pacemaker. For example, certain commercial embodiments of pacemakers are multiprogrammable, rate-responsive pacemakers having the following programmable parameters: pacing mode, sensitivity, refractory period, pulse amplitude, pulse width, lower and upper rate limits, rate response gain, and activity threshold.

For any of the known rate-responsive pacemakers, it is clearly desirable that the sensor output correlate to as high a degree as possible with the actual metabolic and physiologic needs of the patient, so that the resulting rate-responsive pacing rate may be adjusted to appropriate levels. A piezoelectric activity sensor can only be used to indirectly determine the metabolic need. The physical activity sensed can be influenced by upper body motion. Therefore, an exercise that involves arm motion may provide signals that are inappropriately greater than the metabolic need. Conversely, exercises that stimulate the lower body only, such as bicycle riding, may provide a low indication of metabolic need while the actual requirement is very high.

Minute ventilation ($V_e$) has been demonstrated clinically to be a parameter that correlates directly to the actual metabolic and physiologic needs of the patient. Minute ventilation is defined by the equation:

$$V_e = RR \times VT$$

where RR=respiration rate in breaths per minute (bpm), and VT=tidal volume in liters. Clinically, the measurement of $V_e$ is performed by having the patient breathe directly into a device that measures the exchange of air and computes the total volume per minute. The direct measurement of $V_e$ is not possible with an implanted device. However, measurement of the impedance changes across the thorax can be implemented with an implanted pacemaker. Such a pacemaker is disclosed in U.S. Pat. No. 4,702,253 issued to Nappholz et al. The magnitude of the change of the impedance signal corresponds to the tidal volume and the frequency of change corresponds to respiration rate.

The use of transthoracic impedance to indicate $V_e$ has a significant spurious false positive due to upper body myopotential interference and postural changes. Further, slow-acting physiologic parameters such as transitory blood chemistry changes also impact the impedance amplitude. Therefore, it may be desirable to define a rate response function f which minimizes the effects of spurious or transitory changes in impedance sensor output which do not accurately indicate the patient's metabolic needs. U.S. Pat. No. 5,271,395 (Wahlstrand et al.) describes a pacemaker having an impedance-based minute ventilation sensor and another type of sensor (e.g., energy, pressure or other activity sensor), and the pacemaker computes a target rate-responsive pacing rate based upon a function of the two sensors' output.

Wahlstrand et al. additionally determined that basing the pacing rate solely on $V_c$ does not provide the optimum pacing rate increase at the onset of exercise. The VT and RR have an inherent physiologic time delay due to the response of the $CO_2$ receptors and the automatic nervous system. The increase in $V_c$ lags behind the need for the increased cardiac output. Therefore, it was desirable to implement a rate response function $f$ that is based on a combination of a fast responding sensor such as an activity sensor and a physiologically delayed metabolic sensor such as $V_c$.

The combination of the activity and $V_c$ sensor outputs for a rate response function in a manner where the faster of the two independently derived target pacing rates would be utilized as the actual pacing rate is believed to be effective. Such an "OR" combination of sensor signals is disclosed, for example, in U.S. Pat. No. 5,063,927 issued to Webb et al. Provisions in the rate response function $f$ of Wahlstrand included lower and upper rate limits, along with a mapping function from impedance to pacing rate that could be adjusted by a physician to optimize the function for each patient.

The pacemaker function which is most important and which is almost universally programmed is rate. Most pacemakers are preset by the manufacturers at about 65 beats per minute, but may be programmable for rates between 30 and 120 beats per minute. Because the increase in cardiac output that occurs normally with exercise or stress involves not only an increase in heart rate, but also may involve increases in stroke volume, rate alone is not the only applicable measurement for the needs and supply to the patient.

It is known that pacemaker rate is commonly decreased to allow the emergence of a patient's spontaneous rhythm (*A Practical Guide to Cardiac Pacing*, H. Weston Moses et al., Second Ed., Little Brown and Co., 1983, pp. 60–61). There is no specific detail on the relationship of intrinsic heart rate efficiency and target rates in the selection of specific sensing rates for initiation of paced target rates.

SUMMARY OF THE INVENTION

The present invention comprises a pacemaker which is programmed to pace at a preselected lower rate hysteresis and which pacemaker has a sensing means which evaluates an actual metabolic or physiologic need of the patient or a secondary physiological effect (e.g., motion or respiration) which is assumed to correlate to the actual metabolic and physiologic needs of the patient, and the pacemaker being programmable and programmed to change the pacing rate in a hysteresis cycle when the sensing means identifies that the patient requires a higher pacing then the real time pulsing of the cardiovascular system is providing. The sensing means takes measurements or evaluates signals in a preset manner, such as for each cardiac cycle (with a specific activity in that cycle, such as the atrial contraction, the ventricle contraction, etc.), for a predetermined sequence in the cardiac cycle (e.g., alternative specific activities, or sequences of activities, such consecutive sets of atrial and ventricle contractions), or for specific non-cardiac activities which have been established as identifying needs of the actual metabolism and physiology of the patient. The pace rate of the pacemaker is determined by the measurements of the non-cardiac activities (such as specific gas concentrations in the blood, pH levels in the blood, specific types of body movements as shown above to be measured by piezoelectric devices, rate of expiration, etc.) And then comparing these measurements of non-direct cardiac activities to pre-established relationships between the actual metabolic and physiologic needs of the patient and these measurements and then establishing the pacing rate hysteresis which is related to the specific type and value of measurement provided. As these measurements of the non-direct (i.e., no direct measurement of cardiac activity such as pulse or specific contraction is used to establish the pacing rate) can be performed in a continuous manner and compared to each natural cardiac pulse rate, a hysteresis rate may be automatically established by the microchip in the pacemaker in a continuous manner while the activities of the patient are changing.

GENERAL DEFINITIONS OF TERMS IN THE PRESENT INVENTION

"A" represents the term atrial.

"V" represents the term ventricular.

"Ventricular-Sense" or "V-sense" is the act or function of a pacemaker (PM) sensing the (electrical) activity of the ventricle(s), which electrical activity is usually followed by a contraction.

"V-event" is either a V-pace or V-sense.

"Cardiac Cycle" or "CC" is the measurement or interval between similar V-events (e.g., from one V-event to the next V-event) unless otherwise stated.

"Escape Interval" is the duration of a Cardiac Cycle. The Escape Interval starts with a V-sense or a V-pace, and ends with a V-pace, unless specifically stated otherwise.

"Escape Rate" is equal to 60,000÷Escape Interval. The sixty thousand (60,000) represents the number of milliseconds in a minute, and the formula converts the escape interval into the number of Cardiac Cycles per minute.

"Lower Rate" is the lowest rate at which a particular Pacemaker will continuously pace in the absence of intrinsic events. This is usually a programmed value.

"Rate Hysteresis" is an indication that the escape rate is a function of the history of the rate (e.g., programmatically or mathematically related in function). For example, if the last event was a pace pulse, the Escape rate for the next Cardiac Cycle is equal to the programmed value of Lower rate. If the last event was a sense, the Escape rate is lower than the Lower Rate by a predetermined amount (e.g., 10 pulses per minute). The Rate Hysteresis is often expressed as a difference in quantity or a fixed quantity in pulses per minute (ppm). The total interval is referred to as the Hysteresis Interval (HI) and its inverse analogy is referred to as the Hysteresis Rate (HR).

"Sensor Rate" is an Escape Rate value which is a function of the Sensor. Some examples of Sensors are accelerometers, minute ventilation, piezoelectrics (e.g., U.S. Pat. No. 4,428,378), cardiac pressure (as in dP/dT), impedance plethysmography, QT-interval, $O_2$ saturation, etc.

The mode of pacemaker operation is based upon the operation of the sensing, triggering, and inhibition focus of the pacemaker. The pacemaker may operate where the sensor device senses during each cardiac cycle. The pacemaker may also operate by the sensor device sensing during specific patterns of cardiac cycles, such as alterantive pulses or cardiac cycles, every third, fourth, fifth or tenth cardiac cycle, and the like. This pattenmed sensing can reduce the influence of a single anomalous sense (e.g., the vibrations from a single stumbling step, or a quick, short term adrenal flow response).

The three or four stati of the pacemaker are Pace, Sense, and Operating Algorithm. The first two stati are expressed as A (Atrial), V (Ventricle) or D (Dual, both atrial and ventricular). The third operating status may be T for triggered, I for inhibited, or D (for both T and I). Cf *Moses*, 4th ed. pp.100. A fourth letter in the description, such as R which indicates Rate response, is used to describe an additonal feature of the pacemaker. The DDDx mode means either the DDDR or DDD mode.

DETAILED DESCRIPTION OF THE INVENTION

Figure 1:
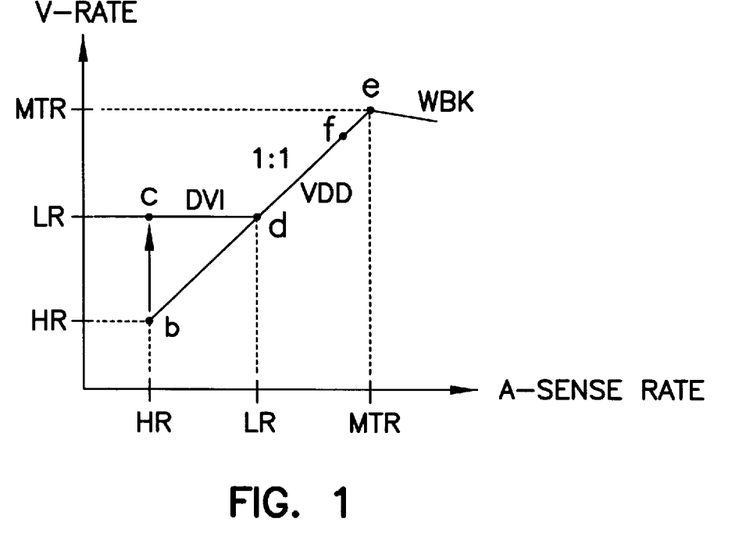
FIG. 1 is a graph of the basic Transfer Function of a pacemaker in DDDx mode with Hysteresis.

The hysteresis loop is a conventional diagrammatic representation of one type of operation of a pacemaker. Looking at FIG. 1, a graph is shown of the Transfer Function in a pacemaker with the A-sense rate shown as the abscissa and the V-sense rate shown as the ordinate. This FIG. 1 shows the basic transfer function of a pacemaker in DDDx mode with hysteresis. In the atrial tracking range of operation of the pacemaker (point b to point e in FIG. 1), there is 1:1 tracking between A-sense and a V-pace. That is, each A-sense is followed by a V-pace, one AV (Atrial-Ventricular) delay interval later, i.e., operation is VDDx behavior. If the A-sense rate were gradually reduced from point f until it was at point b, the V-paces would track the A-senses 1:1 over this range. When the A-sense rate became lower than the Hysteresis rate (point b), the pacemaker system would switch to an escape rate equal to the Lower Rate (point c). There can be one or more A-paces at the point b, which causes the switch to the V-rate at point c. The operating behavior would now be DVI, that is, an A-pace followed by a V-pace at the Lower rate.

As the A-sense rate is increased from point c, the Escape rate would stay at the Lower Rate until the A-sense rate reached point d. Thereafter, the Escape Rate would follow the 1:1 curve, past the point f and up to point e.

For A-sense rates beyond point c, almost all modern DDD pacemakers have an "electronic Wenkebach" (WBK) behavior. This region of operation is not directly related to the operation of the present invention.

The triangle defined by points b–c–d is referred to as the hysteresis loop. The length of the line b–c is usually expressed as a constant value of rate (ΔHR). The length of the line could also be expressed as a function of the rate or as a function of the interval, such as a percentage of the interval.

Figure 2:
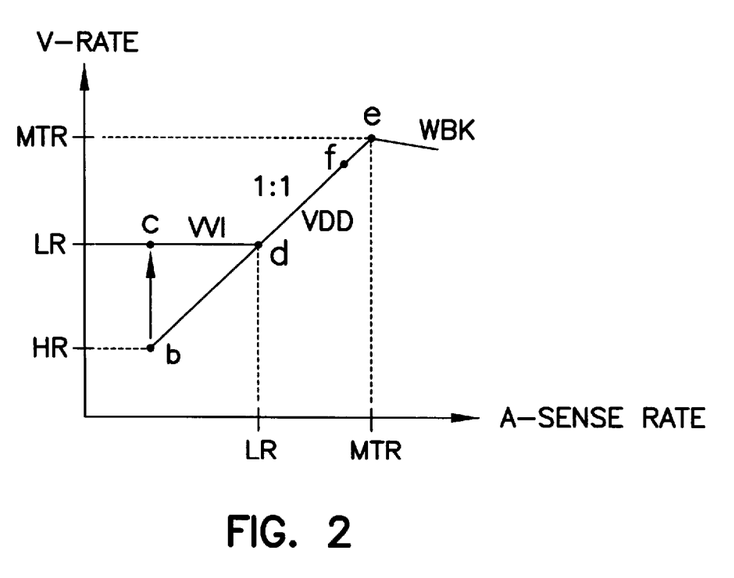
FIG. 2 is a graph of the basic Transfer Function of a pacemaker of VDD mode with Hysteresis.

FIG. 2 illustrates the basic transfer function of VDD mode with hysteresis. Operation of the transfer function is similar to that described with reference to FIG. 1 in describing the function of the DDDx Transfer Function, except that the behavior on the line defined by points c–d is VVI (e.g., U.S. Pat. No. 4,363,325) rather than DVI.

Figure 3:
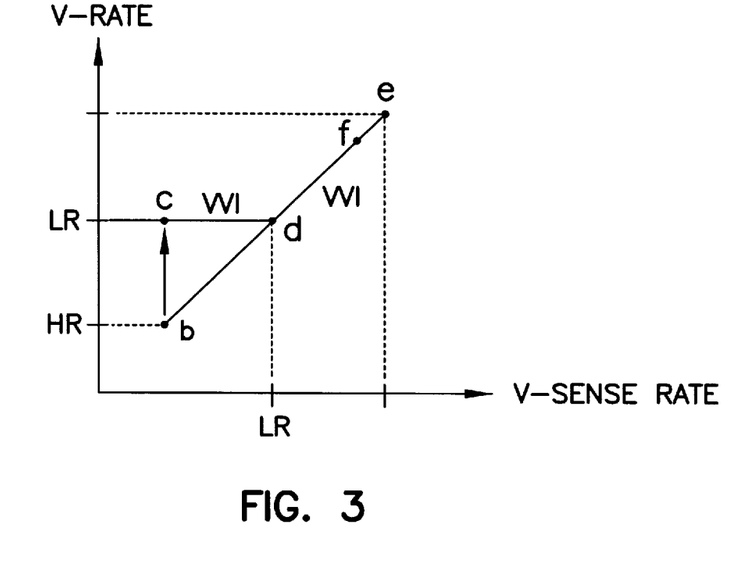
FIG. 3 is a graph of the VVI Transfer Function of a pacemaker.
Figure 4:
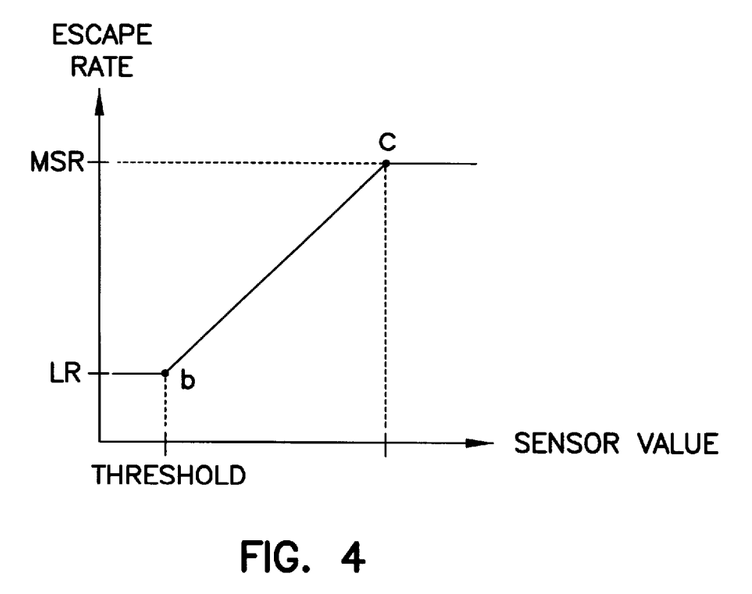
FIG. 4 is a graphic illustration of a Transfer Function by which a Sensor Escape Rate is determined from a Sensor Value (SV).

FIG. 3 illustrates the VVI Mode Transfer Function. It is similar to the VVD Mode Transfer Function except that the abscissa is labeled V-sense Rate, and there is no WBK behavior region. The extension to an AAI Transfer Function is accomplished by simply changing the "V" to "A" in the labels. The Gobeli Lower rate Hysteresis method (e.g., U.S. Pat. No. 3,656,487) applies to the VVI Mode FIG. 4 graphically illustrates how the Sensor Escape rate is derived from the Sensor Value (SV). For very low values of SV, the Escape rate is equal to the Lower Rate (LR). As the SV increases past the "Threshold" value, this increase in the SV causes the Escape Rate to start to increase. The relationship of this increase to the increase in the SV is often linear, but other relationships are known to have clinical value. The portion of the curve between points b and c is referred to as the Response. The slope of the response, the rate of change in the Escape Rate in response to a change in the Sensor Value (dER/dSV), is usually programmable. In FIG. 4, the Escape Rate continues to increase as the SV increases, until the Escape Rate is truncated (limited) at a predetermined value called the maximum Sensor Rate (MSR). This is also usually a programmable value.

Figure 5:
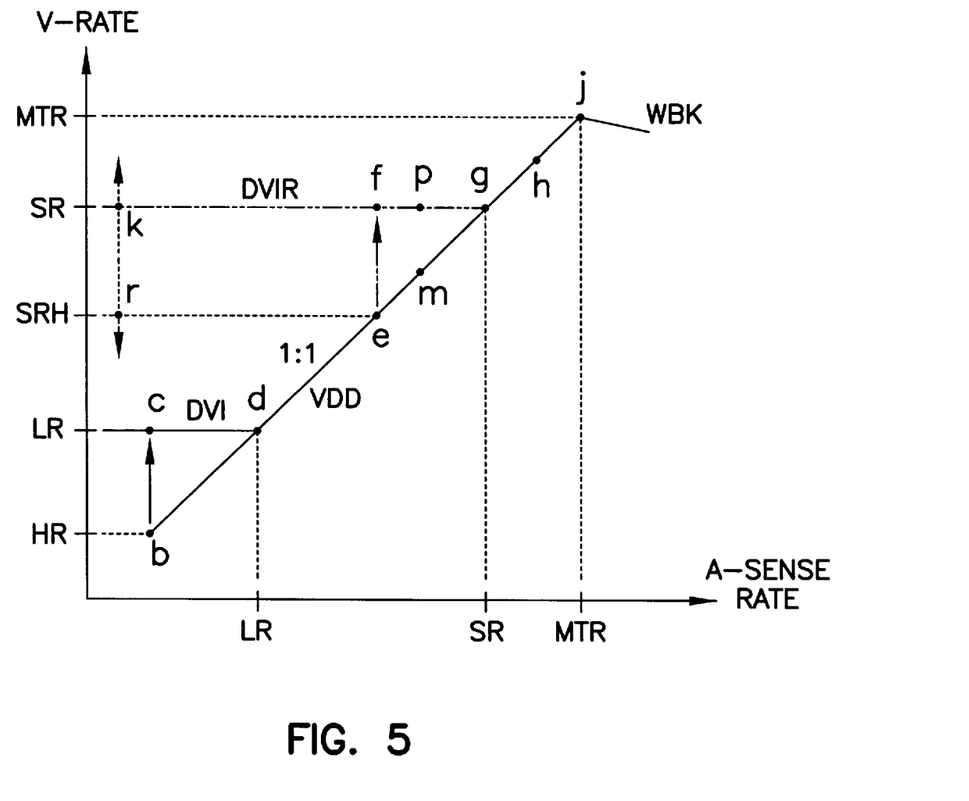
FIG. 5 illustrates by graphic representation Sensor Rate Hysteresis in a pacemaker in the DDDR Mode.

FIG. 5 illustrates Sensor Rate Hysteresis in DDDR Mode according to the practice of the present invention. The graph is derived from FIGS. 1 and 4. If the Sensor Rate (SR) is less than the Lower Rate (LR), the behavior of the pacemaker system is like that in FIG. 1. If the SV increases, the SR will then increase. This results in line g–k being located at a higher point in the graph as illustrated in FIG. 5. In real terms, this indicates that the Sensor Rate can be much higher than the A-pulse rate, and the actual demands of the patient may not be met by the atrial function. If the A-sense Rate was reduced from point h, the V-rate will track the A-sense Rate past point g and down to point e. For A-sense Rates below point e, the behavior of the pacemaker will switch to point f. Pacing behavior will be DVIR with an Escape Rate equal to the SR. As the A-sense Rate is reduced further, the operation of the pacemaker will follow line f–k. If the A-sense rate were to increase, operation of the pacemaker would follow line k–g. For A-sense Rates above g, the operation of the pacemaker will follow line g–j.

Line e–f is the amount of Sensor Rate Hysteresis. It is often expressed as a delta value of rate, but other values as described above for Lower Rate Hysteresis may also be used. The triangle described by e–f–g is the Sensor Rate Hysteresis loop. Note that the lines k–g and c–f shift up and down with the Sensor Value. If the system is operating at point p and the Sensor Rate was reduced, operating behavior would remain as DVIR until the Sensor Rate reached point m. At point m, behavior would switch to VDDR, and as the SR continued to decrease, operation of the pacemaker would follow line m–b. At point b, the operation of the pacemaker would switch back up to point c Another way in which the operation of the pacemaker can switch from point p to point m is by way of an intrinsic rate "Search." This function is accomplished by temporarily (this can be programmed for the interval, e.g., 0.25 min., 0.50 min., 60 min., 6 hours, etc.) switching the Escape Rate from the Sensor Rate to the Sensor Hysteresis Rate for one or more Cardiac Cycles. If the intrinsic underlying rhythm in FIG. 5 is at point m, the Escape Rate would remain adjusted or switched to the Sensor Hysteresis Rate. If the Search function had been initiated while the A-sense rate was at point k, the Search function would have failed to find an intrinsic underlying rhythm during the Search. During the Search, the Escape Rate would be the SHR, and operation would be at point r. This would be an indication of insufficient underlying cardiac activity and the pacemaker would then switch the Escape Rate back to the Sensor Rate, and the operation of the pacemaker would switch back to point k.

The above discussion describes Rate Hysteresis which applies to setting the Escape Rate for the next Cardiac Cycle. VDDx Mode can also conveniently apply Rate Hysteresis to the Cardiac Cycle in progress, that is the current Cardiac Cycle. This can be accomplished by:

1) If the A-sense occurs during the VA-Escape Interval, the V-pace properly tracks the Escape Rate (e.g., U.S. Pat. No. 4,363,325).

2) If the A-sense occurs after the VA-Escape Interval, the V—V interval is extended by the amount of the latency, that is the AV delay timer is restarted. (The term "V-A Escape Interval" applies to interval timers which could be inside of the pacemaker. It is here used as a figure of speech to facilitate instruction of the concept without limiting practice of the invention. Obviously there is no clinical V-A escape in VDD Mode because there is no A-pace.) This restarting assures that the AV interval is the effective value, thus assuring the higher cardiac output associated with the "atrial kick." As the latency of the A-sense continues to increase, the V—V interval has the same increase until the VA Interval is equal to the Escape Rate Interval. At this time, a VVI Escape V-pace occurs. The result of this operation is an Escape rate Hysteresis which can be applied to the Lower Rate or to the Sensor Rate. In this case the amount of the hysteresis is equal to the AV interval.

It is not necessary to restrict the amount of hysteresis to the effective AV interval. Rather than restarting the AV counter, the counter could be set to a variety of values to optimize the system functions, such as CO. Such optimizations are clinically important for the treatment of CHF.

The present invention is in part based upon a consideration of the finding that at an absolute rate (e.g., 70 beats per minute), the actual cardiac efficiency (cardiac output) is higher for the intrinsic sequence of heart activation then for a paced sequence of heart activation. The difference in this efficiency is so significant that the cardiac output for an unpaced sequence of beats at 60 beats per minute provides the cardiac output of a paced cardiac system at 70 beats per minute. The present invention attempts to take advantage of these natural efficiencies by adjusting the escape rate to a level which is nearly equivalent to or less than the effective cardiac output at a preselected pace rate. Also, by favoring the intrinsic rythm over the wider range, the quantity of pace pulses is reduced, reducing battery consumption and extending pacemaker longevity.

What is claimed:

1. A programmable single or dual chamber pacemaker comprising a sensing device, said sensing device providing signals indicating a level of cardiac activity to said pacemaker, said pacemaker having a Lower Rate Hysteresis and a Sensor Rate Hysteresis, with at least one of a V-sense Rate and an A-sense Rate, and said signals being capable of causing said pacemaker to operate with a hysteresis loop in which at least one of A-sense-rate and V-sense rate is at a higher rate than the A-sense rate or the V-sense rate of said Lower Rate Hysteresis or said Sensor Rate Hysteresis.

2. The pacemaker of claim 1 wherein the pacemaker is a dual chamber pacemaker operating in DDDR mode.

3. The pacemaker of claim 2 wherein said sensing device senses during each cardiac cycle.

4. The pacemaker of claim 1 wherein said sensing device senses during specific patterns of cardiac cycles.

5. The pacemaker of claim 1 wherein said sensing device senses during each cardiac cycle.

6. The pacemaker of claim 1 wherein there is more than one programmable function of the relationship dEscape Rate/dSensor Value.

7. The pacemaker of claim 1 wherein a search capability for intrinsic cardiac activity is also included within said pacemaker.

8. The pacemaker of claim 1 wherein the pacemaker is operating in VDDR mode.

9. The pacemaker of claim 1 wherein escape rate hysteresis applies to a cardiac cycle in process during VDD mode for at least one of lower rate hysteresis and sensor rate hysteresis.

10. The pacemaker of claim 1 wherein escape rate hysteresis applies to a cardiac cycle in process during VDD mode for at least one of lower rate hysteresis and sensor rate hysteresis.

11. The pacemaker of claim 1 operating in AAIR or VVIR mode.

12. A programmable single or dual chamber pacemaker comprising a sensing device, said sensing device providing signals indicating a level of cardiac activity to said pacemaker, said pacemaker having a Lower Rate Hysteresis with a V-Rate and an A-Rate, said Lower Rate Hysteresis defining a hysteresis loop in FIG. 5 defined by triangle bcd, said pacemaker upon identifying a sensor rate outside of said triangle bcd such as point g, establishing a Sensor Rate Hysteresis in the form of a hysteresis loop defined in FIG. 5 by triangle efg.

13. The pacemaker of claim 12 wherein said identifying a sensor rate is identifying a piezoelectric response.

14. The pacemaker of claim 13 wherein said sensing device senses during each cardiac cycle.

15. The pacemaker of claim 13 wherein a search capability for intrinsic cardiac activity is also included within said pacemaker.

16. The pacemaker of claim 15 wherein the length of the line bc is different from the length of the line ef so that the ΔHysteresis Rate is different in the Lower Rate Hysteresis and the Sensor Rate Hysteresis.

17. The pacemaker of claim 12 wherein said sensor is an accelerometer and the pacemaker is a dual chamber pacemaker.

18. The pacemaker of claim 17 wherein a search capability for intrinsic cardiac activity is also included within said pacemaker.

19. The pacemaker of claim 12 wherein said pacemaker is a dual chamber pacemaker operating in a DDDR Mode.

20. The pacemaker of claim 12 which is a dual chamber pacemaker wherein said sensing device senses during each cardiac cycle.

21. The pacemaker of claim 12 wherein a search capability for intrinsic cardiac activity is also included within said pacemaker.

22. The pacemaker of claim 21 wherein the length of the line bc is the same as the length of the line ef so that the ΔHysteresis Rate is the same in the Lower Rate Hysteresis and the Sensor Rate Hysteresis.

23. The pacemaker of claim 12 wherein the length of the line bc is the same as the length of the line ef so that the ΔHysteresis Rate is the same in the Lower Rate Hysteresis and the Sensor Rate Hysteresis.

24. The pacemaker of claim 12 wherein the length of the line bc is different from the length of the line ef so that the ΔHysteresis Rate is different in the Lower Rate Hysteresis and the Sensor Rate Hysteresis.

25. The pacemaker of claim 12 wherein there is more than one programmable function of the tracking relationship dEscape Rate/dSensor Value.

26. The pacemaker of claim 12 wherein said pacemaker is implanted in a patient.

27. The pacemaker of claim 12 wherein said pacemaker is external to a patient.

28. The pacemaker of claim 12 operating in AAIR or VVIR mode.

29. A defibrillator which is capable of providing a shock to the heart to defibrillate said heart, said defibrillator also including a pacemaker according to claim 1.

30. The defibrillator of claim 29 wherein said defibrillator is implanted in a patient.

31. The defibrillator of claim 29 wherein said defibrillator is external to a patient.

32. A defibrillator which is capable of providing a shock to the heart to defibrillate said heart, said defibrillator also including a pacemaker according to claim 12.

Figure 6:
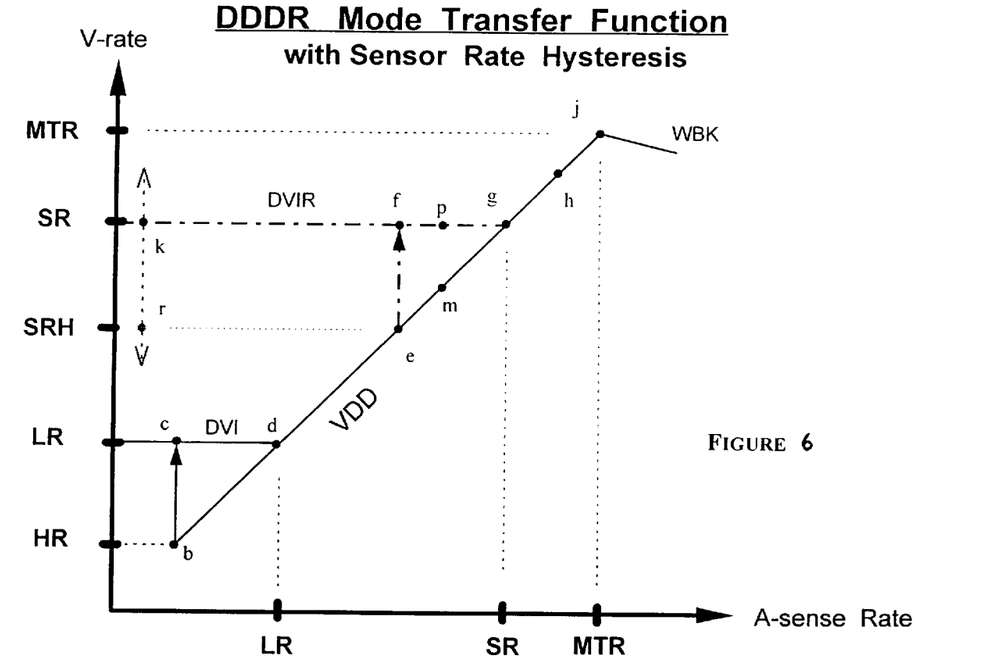
FIG. 6 shows by graphic representation Sensor Rate Hysteresis in a pacemaker in the DDDR mode.

33. A programmable single or dual chamber pacemaker comprising a sensing device, said sensing device providing signals indicating a level of cardiac activity to said pacemaker, said pacemaker having a Lower Rate Hysteresis with a V-Rate and an A-Rate, said Lower Rate Hysteresis defining a hysteresis loop in FIG. 6 defined by triangle bcd, said pacemaker upon identifying a sensor rate outside of triangle bcd, establishing a Sensor Rate Hysteresis in the form of a hysteresis loop defined in FIG. 6 by triangle efg.

34. The pacemaker of claim 33 wherein said identifying a sensor rate is identifying a piezoelectric response.

35. The pacemaker of claim 33 wherein said sensing device senses during each cardiac cycle or during specific patterns of cardiac cycles.

* * * * *

UNITED STATES PATENT AND TRADEMARK OFFICE
CERTIFICATE OF CORRECTION

PATENT NO.: 5,891,175

DATED: April 6, 1999

INVENTOR(S): Walmsley et al.

It is certified that error appears in the above-identified patent and that said Letters Patent is hereby corrected as shown below:

In the Assignee name insert --Inc.,-- after "Cardiac Pacemakers,", therefore.

In column 8 lines 17-20 delete all of claim 9, therefore.
On the title page, "35 claims" should read --34 claims--.

Signed and Sealed this

Thirteenth Day of June, 2000

Attest:

Q. TODD DICKINSON

Attesting Officer

Director of Patents and Trademarks